US008343975B2

(12) United States Patent
Zhang et al.

(10) Patent No.: US 8,343,975 B2
(45) Date of Patent: Jan. 1, 2013

(54) 4-AMINO-3-(IMIDAZOLYL)-PYRAZOLO[3,4-D]PYRIMIDINES

(76) Inventors: Penglie Zhang, Foster City, CA (US); Yibin Zeng, Foster City, CA (US)

(*) Notice: Subject to any disclaimer, the term of this patent is extended or adjusted under 35 U.S.C. 154(b) by 233 days.

(21) Appl. No.: 12/557,428

(22) Filed: Sep. 10, 2009

(65) Prior Publication Data

US 2010/0069396 A1 Mar. 18, 2010

Related U.S. Application Data

(60) Provisional application No. 61/096,191, filed on Sep. 11, 2008.

(51) Int. Cl.
A61K 31/497 (2006.01)
C07D 487/00 (2006.01)
(52) U.S. Cl. .................................. 514/252.16; 544/262
(58) Field of Classification Search .................. None
See application file for complete search history.

(56) References Cited

U.S. PATENT DOCUMENTS

| | | | |
|---|---|---|---|
| 4,238,497 A | 12/1980 | Black et al. | |
| 4,443,466 A | 4/1984 | Karjalainen et al. | |
| 4,927,942 A | 5/1990 | Speranza et al. | |
| 7,157,464 B2 | 1/2007 | Pennell et al. | |
| 7,435,830 B2 | 10/2008 | Pennell et al. | |
| 7,435,831 B2 | 10/2008 | Chen et al. | |
| 7,449,576 B1 | 11/2008 | Pennell et al. | |
| 7,524,845 B2 | 4/2009 | Zhang et al. | |
| 7,576,218 B2 * | 8/2009 | Zhang et al. | 546/211 |
| 7,589,199 B2 | 9/2009 | Pennell et al. | |
| 7,629,344 B2 | 12/2009 | Li et al. | |
| 7,777,035 B2 | 8/2010 | Zhang et al. | |
| 7,842,693 B2 | 11/2010 | Pennell et al. | |
| 2004/0082571 A1 | 4/2004 | Pennell et al. | |
| 2004/0162282 A1 | 8/2004 | Pennell et al. | |
| 2005/0234034 A1 | 10/2005 | Pennell et al. | |
| 2005/0256130 A1 | 11/2005 | Pennell et al. | |
| 2006/0074121 A1 | 4/2006 | Chen et al. | |
| 2006/0106218 A1 | 5/2006 | Pennell et al. | |
| 2007/0010523 A1 | 1/2007 | Zhang et al. | |
| 2007/0010524 A1 | 1/2007 | Zhang et al. | |
| 2007/0254915 A1 | 11/2007 | Leleti et al. | |
| 2008/0058341 A1 * | 3/2008 | Zhang et al. | 514/252.16 |
| 2009/0252779 A1 | 10/2009 | Zhang et al. | |
| 2010/0113472 A1 | 5/2010 | Dairaghi et al. | |
| 2010/0240618 A1 | 9/2010 | Pennell et al. | |

FOREIGN PATENT DOCUMENTS

| | | |
|---|---|---|
| WO | WO 03/105853 A1 | 12/2003 |
| WO | WO 2005/056015 A1 | 6/2005 |
| WO | WO 2005/084667 A1 | 9/2005 |
| WO | WO 2007/002293 A2 | 1/2007 |
| WO | WO 2007/002667 A2 | 1/2007 |
| WO | WO 2007/027734 A2 | 3/2007 |
| WO | WO 2008/147822 A1 | 12/2008 |
| WO | WO 2010/030815 A1 | 3/2010 |
| WO | WO 2010/051561 A1 | 5/2010 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Bedke et al., "Beneficial Effects of CCR1 Blockade on the Progression of Chronic Renal Allograft Damage," Am J Transplant, Mar. 2007; 7(3): pp. 527-537, Epub Jan. 4, 2007.
Bendele et al., "Animal Models of Arthritis: Relevance to Human Disease," Toxicologic Pathology, 1999, vol. 27, No. 1, pp. 134-142.
Bendele et al., "Efficacy of Sustained Blood Levels of Interleukin-1 Receptor Antagonist in Animal Models of Arthritis," Arthritis & Rheumatism, Mar. 1999, vol. 42, No. 3, pp. 498-506.
Borregaard et al., "Evaluation of the effect of the specific CCR1 antagonist CP-481715 on the clinical and cellular responses observed following epicutaneous nickel challenge in human subjects"Contact Dermatitis, 2008 59(4): pp. 212-219.
Clucas et al., "Phase I Evaluation of the Safety, Pharmacokinetics and Pharmacodynamics of CP-481,715," Clin Pharmacokinet, 2007 46(9), pp. 757-766.
Dairaghi et al., "Chemokine Receptor CCR3 Function Is Highly Dependent on Local pH and Ionic Strength," The Journal of Biological Chemistry, Nov. 7, 1997, vol. 272, No. 45, pp. 28206-28209.
Dairaghi et al., "HHV8-encoded vMIP-I Selectively Engages Chemokine Receptor CCR8," The Journal of Biological Chemistry, Jul. 30, 1999, vol. 274, No. 31, pp. 21569-21574.
Gladue et al., "CCR1 Antagonists: What Have We Learned From Clinical Trials," Curr Top Med Chem., Jun. 11, 2010, vol. 10, pp. 1268-1277 [Epub ahead of print].
Gladue et al., "CP-481,715, a Potent and Selective CCR1 Antagonist with Potential Therapeutic Implications for Inflammatory Diseases," The Journal of Biological Chemistry, 2003, vol. 278, No. 42, pp. 40473-40480.
Gladue et al., "Current Status of CCR1 Antagonists in Clinical Trials," Chemokine Biology—Basic Research and Clinical Application, vol. II, 2007 pp. 103-113.
Gladue et al., "The Human Specific CCR1 Antagonist CP-481,715 Inhibits Cell Infiltration and Inflammatory Responses in Human CCR1 Transgenic Mice," The Journal of Immunology, 2006, vol. 176, pp. 3141-3148.
Hesselgesser et al., "Identification and Characterization of Small Molecule Functional Antagonists of the CCR1 Chemokine Receptor," The Journal of Biological Chemistry, Jun. 19, 1998, vol. 273, No. 25, pp. 15687-15692.
International Search Report mailed on Aug. 6, 2008, for International Application No. PCT/US08/64374 filed on May 21, 2008, 2 pages.
Liang et al., "Identification and Characterization of a Potent, Selective, and Orally Active Antagonist of the CC Chemokine Receptor-1," The Journal of Biological Chemistry, Jun. 23, 2000, vol. 275, No. 25, pp. 19000-19008.
Liang et al., "Species selectivity of a small molecule antagonist for the CCR1 chemokine receptor," European Journal of Pharmacology, 2000, vol. 389, pp. 41-49.

(Continued)

Primary Examiner — Jeffrey Murray
(74) Attorney, Agent, or Firm — Kilpatrick, Townsend & Stockton LLP

(57) ABSTRACT

Compounds are provided that act as potent antagonists of the CCR1 receptor, and have in vivo anti-inflammatory activity. The compounds are 4-amino-3-imidazoyl-pyrazolo[3,4-d] pyrimidine derivatives and are useful in pharmaceutical compositions, methods for the treatment of CCR1-mediated disease, and as controls in assays for the identification of competitive CCR1 antagonists.

4 Claims, No Drawings

OTHER PUBLICATIONS

Melter et al. "Chemokines and their receptors in human clinical solid organ transplantation," Current Opinion in Organ Transplantation, 2002, vol. 7, p. 77-84.

Ng et al., "Discovery of Novel Non-Peptide CCR1 Receptor Antagonists," Journal of Medicinal Chemistry, 1999, vol. 42, No. 22, pp. 4680-4694.

Palmer, A.M., "Pharmacotherapy for Alzheimer's disease: progress and prospects," Trends in Pharmacological Sciences, Sep. 2002, vol. 23, No. 9, pp. 426-433.

Penfold et al., "Cytomegalovirus encodes α potent a chemokine," Proc. Natl. Acad. Sci. USA, Aug. 1999, vol. 96, pp. 9839-9844.

Podolin et al. "A Potent and Selective Nonpeptide Antagonist of CXCR2 Inhibits Acute and Chronic Models of Arthritis in the Rabbit," The Journal of Immunology, 2002, vol. 169, pp. 6435-6444.

Trentham et al., "Autoimmunity to Type II Collagen: An Experimental Model of Arthritis," The Journal of Experimental Medicine, 1977, vol. 146, pp. 857-868.

U.S. Appl. No. 12/432,536, filed Apr. 29, 2009, for Andrew M. K. Pennell et al.

U.S. Appl. No. 12/829,312, filed Jul. 1, 2010, for Penglie Zhang et al.

U.S. Appl. No. 12/952,938, filed Nov. 23, 2010, for Andrew M. K. Pennell et al.

Yun et al. "Combined Blockade of the Chemokine Receptors CCR1 and CCR5 Attenuates Chronic Rejection," Circulation 2004, vol. 109, pp. 932-937.

PCT/US2009/056560, International Search Report and Written Opinion, dated Dec. 23, 2009, 6 pages.

Taylor, E., et al., "3-Cyano-4-aminopyrazolo[3,4-d]pyrimidine. An Azalog of the Aglycone of Toyocamycin," The Journal of Organic Chemistry, Jan. 1966, vol. 31, pp. 342-343.

* cited by examiner

4-AMINO-3-(IMIDAZOLYL)-PYRAZOLO[3,4-D]PYRIMIDINES

CROSS-REFERENCES TO RELATED APPLICATIONS

This application claims the benefit of U.S. Ser. No. 61/096,191 filed Sep. 11, 2008; the entire content of which is incorporated herein by reference.

STATEMENT AS TO RIGHTS TO INVENTIONS MADE UNDER FEDERALLY SPONSORED RESEARCH AND DEVELOPMENT

Not applicable

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., *Semin Immunol* 11(2):95-104 (1999)). A hallmark of some demyelinating diseases such as multiple sclerosis is the chemokine-mediated monocyte/macrophage and T cell recruitment to the central nervous system (see, Kennedy, et al., *J. Clin. Immunol.* 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Bone metabolism is dependent on the overall activity of osteoblasts which control bone formation and osteoclasts which control bone resorption. Abnormality of bone metabolism is considered to be caused by an imbalance of the bone formation and the bone resorption. Osteoporosis (and postmenopausal osteoporosis), hypercalcemia, Paget's disease, renal osteodystrophy, rheumtoidarthritis, osteoarthristis, lytic bone metastases, multiple myeloma and the like are known as diseases accompanying abnormality of bone metabolism. Osteoporosis is a typical disease caused by such abnormality of bone metabolism. This disease is generated when bone resorption by osteoclasts exceeds bone formation by osteoblasts. The disease is characterized by a decrease in both the bone calcified material and the bone matrix. CCR1 is believed to play a role in the recruitment of osteoclast precursors and their maturation, and inhibition of this process may amerliorate the disease (Vallet et al, *Blood,* 110:3744-3752 (2007)). Further sequestration of multiple myeloma cells in the bone marrow leads to the recruitment of osteoclasts to these sites, providing a feedback loop to myeloma proliferation, and stimulating decalcification (Menu et al, *Clin Exp Metastases,* 23:291-300 (2006)).

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., *Ann. Rev. Immunol.* 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., *Current Pharmaceutical Design* 9:1201-1208 (2003)) since they have been implicated in rheumatoid arthritis, transplant rejection (see, DeVries, M. E., et al., ibid.), and multiple sclerosis (see, Fischer, et al., *J. Neuroimmunol.* 110 (1-2):195-208 (2000); Izikson, et al., *J. Exp. Med.* 192(7):1075-1080 (2000); and Rottman, et al., *Eur. J. Immunol.* 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., *Immunol Lett.* 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., *J. Biol. Chem.* 273(25):15687-15692 (1998); Ng, et al., *J. Med. Chem.* 42(22):4680-4694 (1999); Liang, et al., *J. Biol. Chem.* 275(25):19000-19008 (2000); and Liang, et al., *Eur. J. Phar-*

*macol.* 389(1):41-49 (2000)). In view of the effectiveness demonstrated for treatment of disease in animal models (see, Liang, et al., *J. Biol. Chem.* 275(25):19000-19008 (2000)), the search has continued to identify additional compounds that can be used in the treatment of diseases mediated by CCR1 signaling.

BRIEF SUMMARY OF THE INVENTION

The present invention relates to compounds having Formula I:

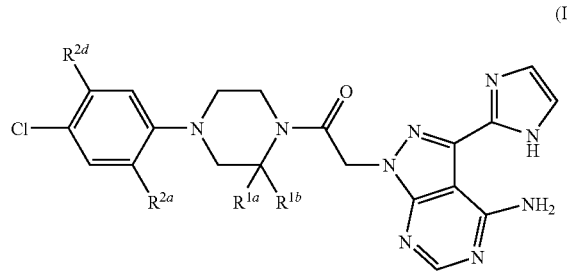

(I)

or pharmaceutically acceptable salts, hydrates or N-oxides thereof. In Formula I, $R^{1a}$ and $R^{1b}$ are each independently selected from H and $CH_3$; $R^{2a}$ selected from H and F; and $R^{2d}$ is selected from H, $C_{1-4}$ alkoxy and $C_{1-4}$ haloalkoxy.

In addition to the compounds provided herein, the present invention further provides pharmaceutical compositions containing one or more of these compounds, as well as methods for the use of these compounds primarily to treat diseases associated with CCR1, CCR2 and/or CCR3 signalling activity.

BRIEF DESCRIPTION OF THE DRAWINGS

NONE

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The terms "alkoxy," is used in their conventional sense, and refer to those alkyl groups attached to the remainder of the molecule via an oxygen atom. Examples of alkoxy groups include methoxy, ethoxy, isopropoxy, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like. Similarly, the term "haloalkoxy," is meant to include monohaloalkoxy and polyhaloalkoxy, such as trifluoromethoxy ($CF_3O$—) and 2-fluoroethoxy ($FCH_2CH_2O$—).

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996). Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (BOC), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Amino acid coupling reagent" refers to a reagent, such as HBTU (O-(benzotriazol-1-yl)-N,N,N',N'-tetramethyluronium hexafluorophosphate), etc., that will react with the carboxylic acid group of an amino acid to form an activated intermediate that can be used to condense with a wide variety of nucleophiles, for example, amines, alcohols and thiols, to produce other esters, thioesters or amides groups.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. General

The present invention derives from the discovery that compounds of Formula I act as potent antagonists of the CCR1 receptor. The compounds have in vivo anti-inflammatory activity and have superior pharmacokinetic properties. Accordingly, the compounds provided herein are useful in pharmaceutical compositions, methods for the treatment of CCR1-mediated diseases, and as controls in assays for the identification of competitive CCR1 antagonists.

III. Compounds

In one aspect, the present invention provides for a compound of Formula I:

(I)

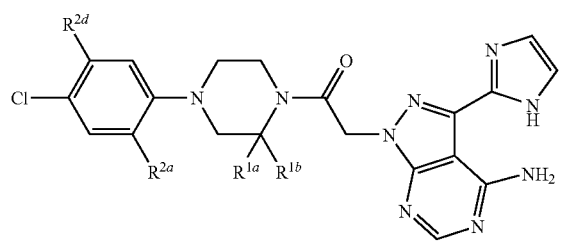

or pharmaceutically acceptable salts, hydrates or N-oxides thereof. In Formula I, $R^{1a}$ and $R^{1b}$ are each independently selected from the group consisting of H and $CH_3$; $R^{2a}$ is selected from the group consisting of H and F; and $R^{2d}$ is selected from the group consisting of H, $C_{1-4}$ alkoxy and $C_{1-4}$ haloalkoxy. In one embodiment, $R^{2a}$ is hydrogen. In another embodiment, $R^{1a}$ and $R^{1b}$ are each H. In another embodiment, $R^{1b}$ is methyl and $R^{1a}$ is H. In yet another embodiment, $R^{1a}$ and $R^{1b}$ are each methyl. In still another embodiment, $R^{2a}$ is hydrogen and $R^{2d}$ is selected from the group consisting of methoxy, ethoxy and trifluoromethoxy.

In one preferred embodiment, the compounds of the invention are of Formula Ia or Ib:

Ia

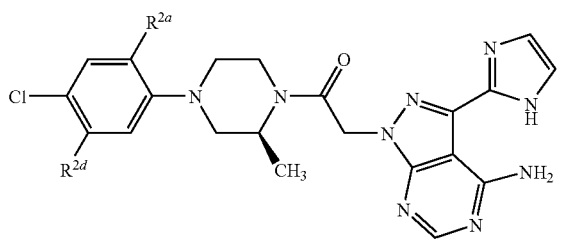

Ib

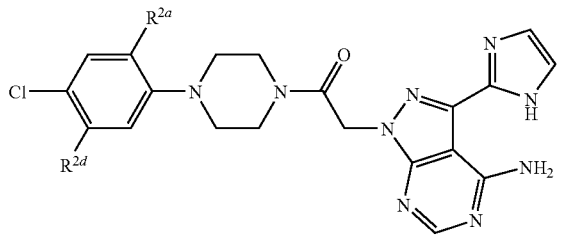

wherein $R^{2a}$ is selected from the group consisting of H and F; and $R^{2d}$ is selected from the group consisting of methoxy, ethoxy and trifluoromethoxy.

In a specific embodiment, compounds of the invention are selected from the group consisting of:

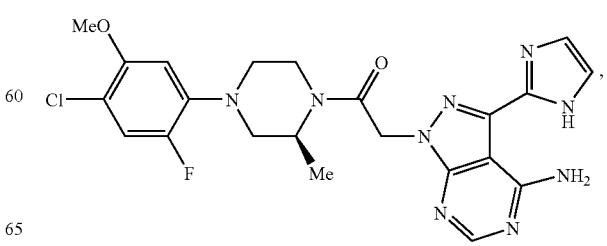

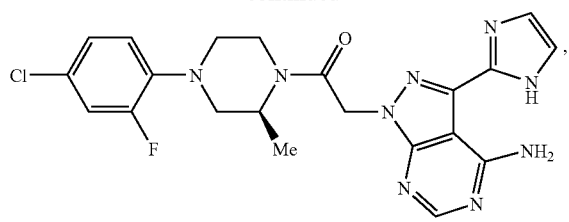

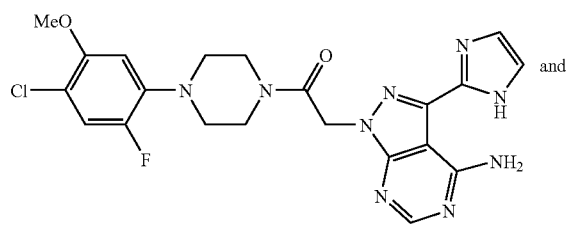

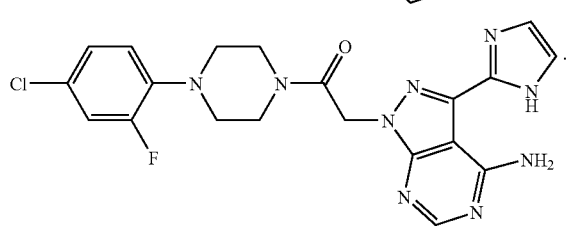

In another specific embodiment, the compounds of the invention are selected from the group consisting of:

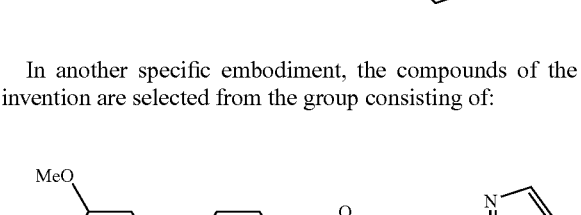

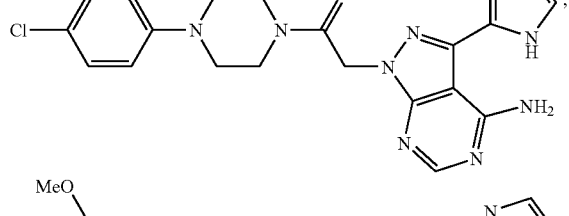

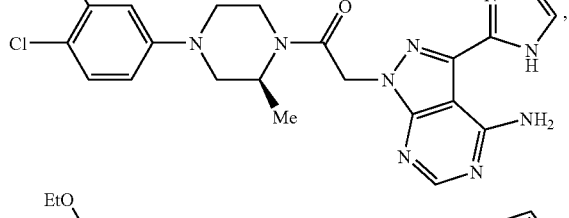

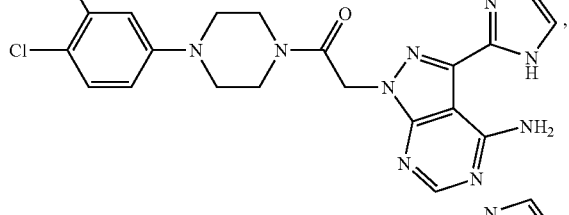

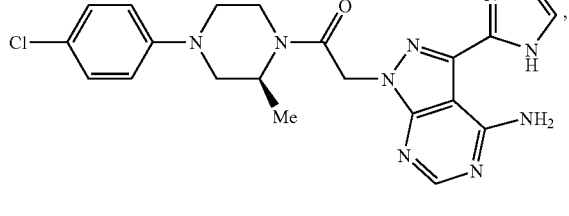

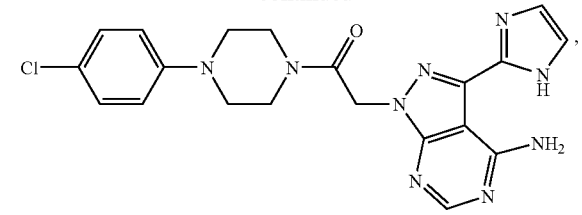

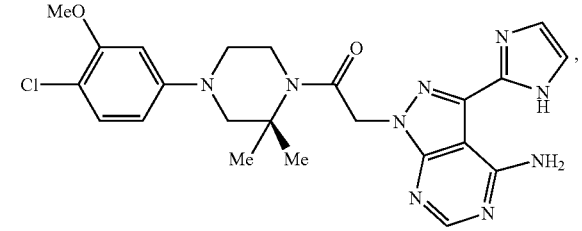

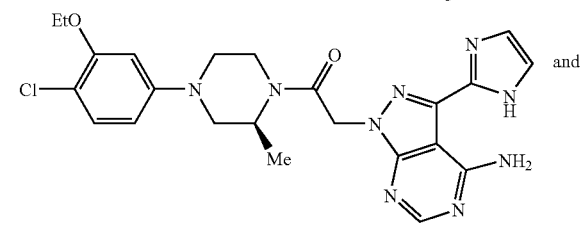

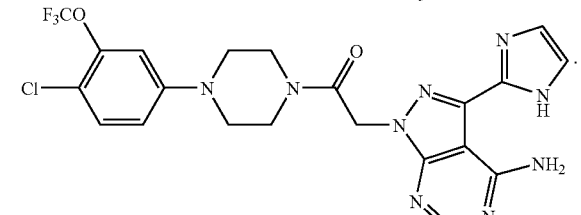

In yet another embodiment, the compound of the invention has the formula:

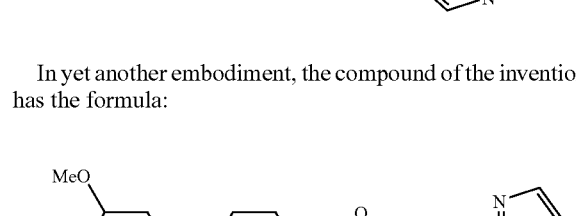

In still yet another embodiment, compounds of the invention of Formula I are selected from the group consisting of the compounds set forth in Table 1.

TABLE 1

(S)-2-(4-amino-3-(1H-imidazol-2-yl)-1H-pyrazolo[3,4-d]pyrimidin-1-yl)-1-(4-(4-chloro-2-fluoro-5-methoxyphenyl)-2-methylpiperazin-1-yl)ethanone
(S)-2-(4-amino-3-(1H-imidazol-2-yl)-1H-pyrazolo[3,4-d]pyrimidin-1-yl)-1-(4-(4-chloro-2-fluorophenyl)-2-methylpiperazin-1-yl)ethanone
2-(4-amino-3-(1H-imidazol-2-yl)-1H-pyrazolo[3,4-d]pyrimidin-1-yl)-1-(4-(4-chloro-2-fluoro-5-methoxyphenyl)piperazin-1-yl)ethanone
2-(4-amino-3-(1H-imidazol-2-yl)-1H-pyrazolo[3,4-d]pyrimidin-1-yl)-1-(4-(4-chloro-2-fluoro-5-methoxyphenyl)piperazin-1-yl)ethanone
(S)-2-(4-amino-3-(1H-imidazol-2-yl)-1H-pyrazolo[3,4-d]pyrimidin-1-yl)-1-(4-(4-chloro-3-methoxyphenyl)-2-methylpiperazin-1-yl)ethanone
2-(4-amino-3-(1H-imidazol-2-yl)-1H-pyrazolo[3,4-d]pyrimidin-1-yl)-1-

TABLE 1-continued (4-(4-chloro-3-ethoxyphenyl)piperazin-1-yl)ethanone
(S)-2-(4-amino-3-(1H-imidazol-2-yl)-1H-pyrazolo[3,4-d]pyrimidin-1-yl)-
1-(4-(4-chlorophenyl)-2-methylpiperazin-1-yl)ethanone
2-(4-amino-3-(1H-imidazol-2-yl)-1H-pyrazolo[3,4-d]pyrimidin-1-yl)-1-
(4-(4-chlorophenyl)piperazin-1-yl)ethanone
2-(4-amino-3-(1H-imidazol-2-yl)-1H-pyrazolo[3,4-d]pyrimidin-1-yl)-1-
(4-(4-chloro-3-methoxyphenyl)-2,2-dimethylpiperazin-1-yl)ethanone
(S)-2-(4-amino-3-(1H-imidazol-2-yl)-1H-pyrazolo[3,4-d]pyrimidin-1-yl)-
1-(4-(4-chloro-3-ethoxyphenyl)-2-methylpiperazin-1-yl)ethanone
2-(4-amino-3-(1H-imidazol-2-yl)-1H-pyrazolo[3,4-d]pyrimidin-1-yl)-1-
(4-(4-chloro-3-(trifluoromethoxy)phenyl)piperazin-1-yl)ethanone
2-(4-amino-3-(1H-imidazol-2-yl)-1H-pyrazolo[3,4-d]pyrimidin-1-yl)-1-
(4-(4-chloro-3-methoxyphenyl)piperazin-1-yl)ethanone Preparation of Compounds The Scheme 1 below, as well as the schemes in the Examples, provide certain synthetic routes that can be followed to access certain compounds of the present invention. Other routes or modifications of the routes presented below would be readily apparent to a skilled artisan and are within the scope of the present invention.

Scheme 1 illustrates the synthesis of a 4-amino-3-imidazolyl substituted pyrazolo[3,4-d]pyrimidines used in a coupling reaction with a substituted piperazine to form the compounds of the present invention. As shown in Scheme 1, hydrazinecarboxylic acid tert-butyl ester and 2,3-dicyanobut-2-enedinitrile can be combined to form the substituted pyrazole compound B (5-amino-1H-pyrazole-3,4-dicarbonitrile). Compound B, upon treatment with, for example, an orthoformate (e.g., trimethylorthoformate) provides intermediate C (shown as (E)-methyl N-3,4-dicyano-1H-pyrazol-5-ylformimidate). Ring closure to form the pyrazolo[3,4-d]pyrimidine shown as compound A (4-amino-1H-pyrazolo[3,4-d]pyrimidine-3-carbonitrile) can be accomplished by treatment of intermediate C with ammonia.

Further elaboration of the pyrazolo[3,4-d]pyrimidine is accomplished by treatment of Compound A with, for example, tert-butyl chloroacetate in the presence of potassium carbonate to obtain (4-amino-3-cyano-pyrazolo[3,4-d]pyrimidin-1-yl)-acetic acid tert-butyl ester, which can then be refluxed with ethylenediamine in the presence of ethanol and acetic acid to produce tert-butyl 2-(4-amino-3-(4,5-dihydro-1H-imidazol-2-yl)-1H-pyrazolo[3,4-d]pyrimidin-1-yl)acetate.

As shown tert-butyl 2-(4-amino-3-(4,5-dihydro-1H-imidazol-2-yl)-1H-pyrazolo[3,4-d]pyrimidin-1-yl)acetate can be oxidized with DMP in the presence of the solvent DMSO to obtain tert-butyl 2-(4-amino-3-(1H-imidazol-2-yl)-1H-pyrazolo[3,4-d]pyrimidin-1-yl)acetate.

Finally, tert-butyl 2-(4-amino-3-(1H-imidazol-2-yl)-1H-pyrazolo[3,4-d]pyrimidin-1-yl)acetate can be treated with HCl in dioxane to obtain a 4-amino-3-imidazolyl substituted pyrazolo [3,4-d]pyrimidine salt (2-(4-amino-3-(1H-imidazol-2-yl)-1H-pyrazolo[3,4-d]pyrimidin-1-yl)acetic acid.2HCl).

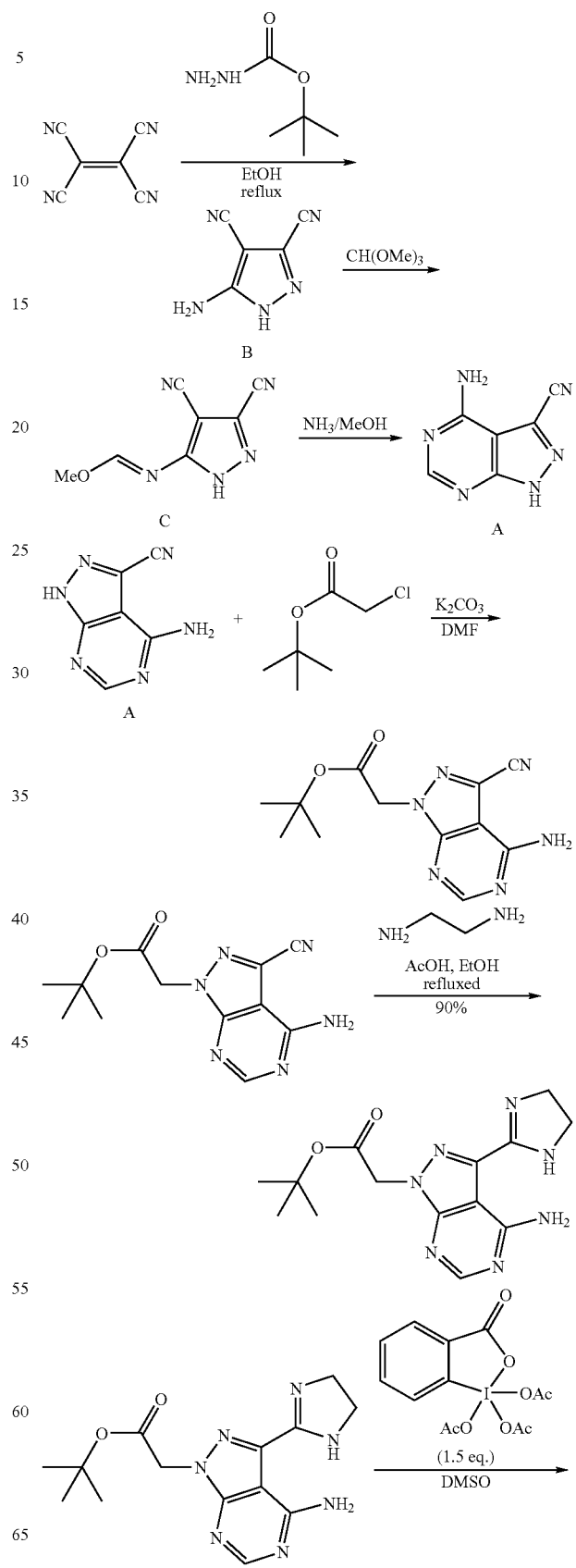

Scheme 1

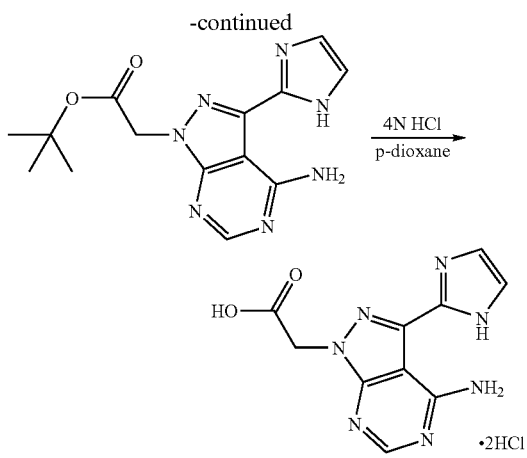

III. Pharmaceutical Compositions

In addition the compounds provided above, the compositions for modulating CCR1, CCR2 and CCR3 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

IV. Methods of Treating Diseases Modulated by CCR1

In yet another aspect, the present invention provides methods of treating CCR1-, CCR2- and/or CCR3-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders, bone disease, cancer and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1, CCR2 or CCR3 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as asthma, allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, Takuyasu arthritis, rheumatoid arthritis, psoriatic arthritis, osteoarthritis, polyarticular arthritis, multiple sclerosis, systemic lupus erythematosus, type I diabetes, type II diabetes, type I diabetes (recent onset), optic neuritis, glomerulonephritis, and the like, (10) graft rejection including allograft rejection and acute and chronic graft-vs-host disease, (11) fibrosis (e.g. pulmonary fibrosis (i.e. idiopathic pulmonary fibrosis, interstitial pulmonary fibrosis), fibrosis associated with end-stage renal disease, fibrosis caused by radiation, tubulointerstitial fibrosis, subepithelieal fibrosis, scleroderma (progressive systemic sclerosis), hepatic fibrosis (including that caused by alcoholic or viral hepatitis), primary and secondary cirrhosis), (12) acute and chronic lung inflammation (chronic obstructive pulmonary disease, chronic bronchitis, adult respiratory distress syndrome, respiratory distress syndrome of infancy, immune complex alveolitis) and (13) other diseases in which undesired inflammatory responses or immune disorders are to be inhibited, such as cardiovascular disease including atherosclerosis, vascular inflammation resulting from tissue transplant or during restenosis (including, but not limited to restenosis following angioplasty and/or stent insertion), other acute and chronic inflammatory conditions such as myositis, neurodegenerative diseases (e.g., Alzheimer's disease), encephalitis, meningitis, hepatitis, nephritis, sepsis, sarcoidosis, allergic conjunctivitis, otitis, sinusitis, synovial inflammation caused by arthroscopy, hyperuremia, trauma, ischaemia reperfusion injury, nasal polyosis, preeclampsia, oral lichen planus, Guillina-Barre syndrome, granulomatous diseases, conditions associated with leptin production, Behcet's syndrome and gout and in wound healing applications (14) immune mediated food allergies such as Celiac disease.

In another group of embodiments, diseases or conditions can be treated with modulators of CCR1 function. Examples of diseases to be treated with modulators of CCR1 function include cancers (both primary and metastatic) (e.g., multiple myeloma; Hata, H., Leukemia & Lymphoma, 2005, 46(7); 967-972), cardiovascular diseases, osteolytic diseases including osteoporosis (and post-menopausal osteoporosis), hypercalcemia, Paget's disease, renal osteodystrophy, rheumtoidarthritis, osteoarthristis, lytic bone metastases, and multiple myeloma, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Pharmaceutical compositions of this invention can also inhibit the production of metalloproteinases and cytokines at inflammatory sites, either directly or indirectly (as a consequence of decreasing cell infiltration) thus providing benefit for diseases or conditions linked to these cytokines.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, rniroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (1) other antagonists of the chemokine receptors, especially CCR5, CXCR2, was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:
DMF, Dimethyl formamide; TFA, Trifluoroacetic Acid; THF, Tetrahydrofuran; EtOAc, Ethyl acetate; BOC$_2$O, di-tertbutyl dicarbonate or BOC anhydride; HPLC, High Pressure Liquid Chromatography; DIPEA, Diisopropyl ethylamine; HCTU, 1-[bis(dimethylamino)methylene]-5-chloro-1H-Benzotriazolium-3-oxide hexafluorophosphate (1-); HBTU, O-(benzotriazol-1-yl)-N,N,N',N'-tetramethyluronium hexafluorophosphate; dppf, 1,1'-Bis(diphenylphosphino) ferrocene; Pd$_2$(dba)$_3$, Tris(dibenzylideneacetone) dipalladium(0); DIPEA, diisopropylethylamine; DMP, dimethylphthalate; Me, methyl; Et, ethyl; DCM, dichloromethane.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent. CXCR3, CCR2, CCR3, CCR4, CCR7, CX3CR1 and CXCR6; (m) lubricants or emollients such as petrolatum and lanolin, (n) keratolytic agents (e.g., tazarotene), (o) vitamin D$_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

V. EXAMPLES

The following examples are offered to illustrate, but not to limit the claimed invention.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP 1100 HPLC equipped with an Agilent Zorbax SB-C18, 2.1×50 mm, 5μ column for sample delivery. Normally the analyte

Example 1

This example illustrates the preparation of 2-[4-amino-3-(1H-imidazol-2-yl)-pyrazolo[3,4-d]pyrimidin-1-yl]-1-[4-(4-chloro-3-methoxyphenyl)piperazin-1-yl]ethanone

Step 1: 4-amino-1H-pyrazolo[3,4-d]pyrimidine-3-carbonitrile

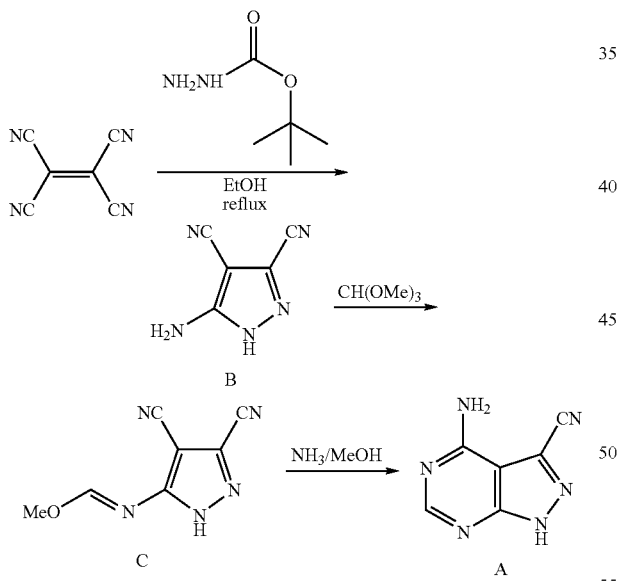

To a solution of hydrazinecarboxylic acid tert-butyl ester (129 g, 0.976 mol) in ethanol (700 mL) placed in an ice bath was added 2,3-dicyano-but-2-enedinitrile (125 g, 0.976 mol) in portions while keeping the internal temperature below 16° C. After the addition was complete, the reaction mixture was heated to reflux for 4 h, concentrated and dried under vacuum to give 5-amino-1H-pyrazole-3,4-dicarbonitrile. MS (ES) m/z 134.1 (M+H$^+$).

5-Amino-1H-pyrazole-3,4-dicarbonitrile obtained above was refluxed in trimethylorthoformate (1 L) for 8 h. The mixture was then concentrated and dried under vacuum to afford N-(4,5-dicyano-2H-pyrazol-3-yl)-formimidic acid methyl ester, which was was dissolved in methanol (400 mL), cooled to 0° C., and treated with 7 N NH$_3$ in methanol (1 L). The resulting mixture was allowed to warm up to room temperature overnight and filtered. The solid was washed with a 2:1 mixture of of MeOH—H$_2$O (100 mL), acetone (100 mL) and ether (100 mL), then dried under vacuum to give 4-amino-1H-pyrazolo[3,4-d]pyrimidine-3-carbonitrile (79 g, 50% yield). MS (ES) m/z 161.0 (M+H$^+$).

Step 2: tert-Butyl 2-(4-amino-3-cyano-1H-pyrazolo[3,4-d]pyrimidin-1-yl)acetate

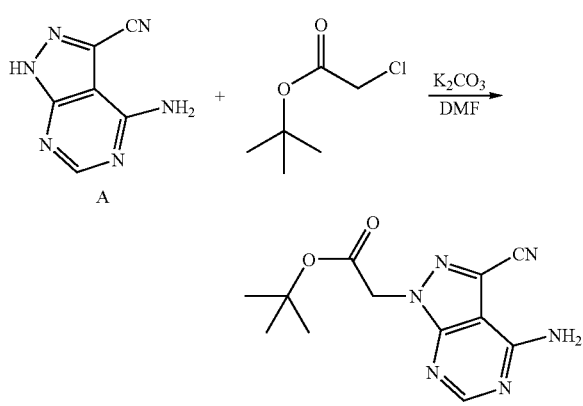

To a mixture of 4-amino-1H-pyrazolo[3,4-d]pyrimidine-3-carbonitrile (76.6 g, 0.476 mol) and potassium carbonate (197 g, 1.427 mmol) in DMF (680 mL) at 0° C. was added tert-butyl chloroacetate (68.1 mL, 0.476 mol) dropwise while maintaining the internal temperature below 20° C. The resulting mixture was stirred for 22 h, filtered and washed with EtOAc (100 mL×2). The solid obtained was suspended in ice water (1.5 L), filtered, washed with ice water (500 mL) and ether (100 mL×2), then dried in vacuo to afford tert-butyl 2-(4-amino-3-cyano-1H-pyrazolo[3,4-d]pyrimidin-1-yl)acetate (81.6 g, 62.3% yield).

MS (ES) m/z 275.0 (M+H$^+$).

Step 3: tert-Butyl 2-(4-amino-3-(4,5-dihydro-1H-imidazol-2-yl)-1H-pyrazolo[3,4-d]pyrimidin-1-yl)acetate

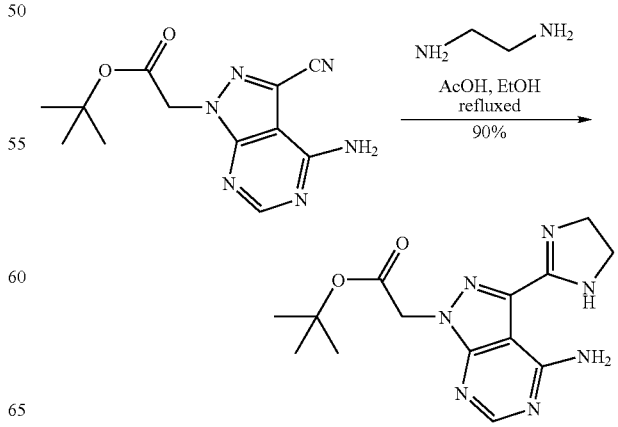

To a mixture of (4-amino-3-cyano-pyrazolo[3,4-d]pyrimidin-1-yl)-acetic acid tert-butyl ester (80 g, 0.291 mol) and EtOH (800 mL) in an ice water bath was added acetic acid (67 mL) and then ethylenediamine (195 mL). The resulting mixture was refluxed for 90 min, cooled to room temperature and filtered. The solid was suspended in water (1 L), filtered and dried in vacuo to give of tert-butyl 2-(4-amino-3-(4,5-dihydro-1H-imidazol-2-yl)-1H-pyrazolo[3,4-d]pyrimidin-1-yl)acetate (84.6 g, 90% yield). MS (ES) m/z 318.1 (M+H$^+$).

Step 4: (2-(4-amino-3-(1H-imidazol-2-yl)-1H-pyrazolo[3,4-d]pyrimidin-1-yl)acetic acid dihydrochloride

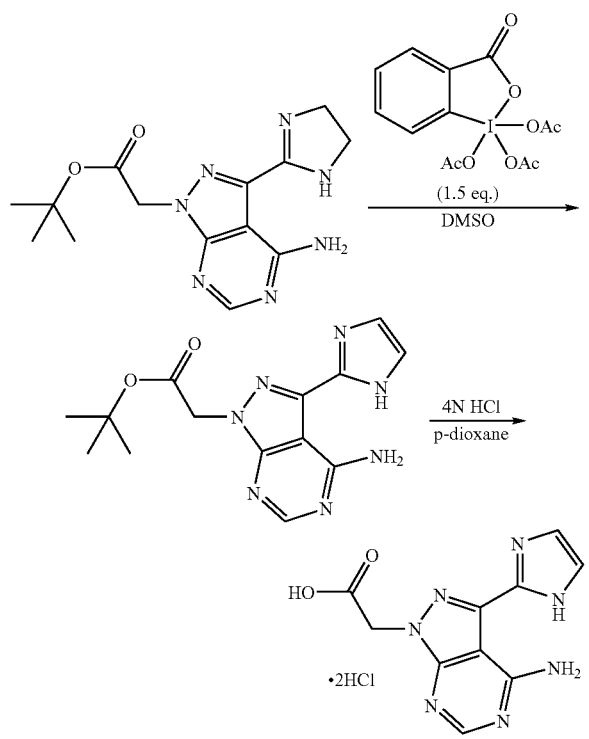

To a mixture of tert-Butyl 2-(4-amino-3-(4,5-dihydro-1H-imidazol-2-yl)-1H-pyrazolo[3,4-d]pyrimidin-1-yl)acetate (84 g, 0.265 mol) and DMSO (900 mL) in an ice water bath was added Dess-Martin periodinane (169.6 g, 0.4 mol) in portions while keeping the internal temperature below 25° C. The mixture was stirred for 2 h at room temperature and then poured into ice water (2 L) which contained 84 g of Na$_2$S$_2$O$_3$. The mixture was adjusted to pH 12-14 with 3 N NaOH and filtered to give a solid, which was washed with water, resuspended in ice-water (2 L), filtered, washed with water (500 mL), EtOAc (100 mL×2) and Et$_2$O (100 mL×2), and dried in vacuo to give (2-(4-amino-3-(1H-imidazol-2-yl)-1H-pyrazolo[3,4-d]pyrimidin-1-yl)acetic acid tent-butyl ester (66.2 g, 80% yield). MS (ES) m/z 316.1 (M+H$^+$).

(2-(4-amino-3-(1H-imidazol-2-yl)-1H-pyrazolo[3,4-d]pyrimidin-1-yl)acetic acid tert-butyl ester (61 g, 193 mmol) was treated with 4 N HCl in dioxane (700 mL) at reflux for 2 h. After cooling to room temperature, the solid was collected by filtration, washed with EtOAc (80 mL×2) and Et$_2$O (100 mL), and dried in vacuo to give (2-(4-amino-3-(1H-imidazol-2-yl)-1H-pyrazolo[3,4-d]pyrimidin-1-yl)acetic acid as a dihydrochloride salt (66 g, quantitative). MS (ES) m/z 260.1 (M+H$^+$).

Step 5: 2-[4-Amino-3-(1H-imidazol-2-yl)-pyrazolo[3,4-d]pyrimidin-1-yl]-1-[4-(4-chloro-3-methoxyphenyl)piperazin-1-yl]ethanone

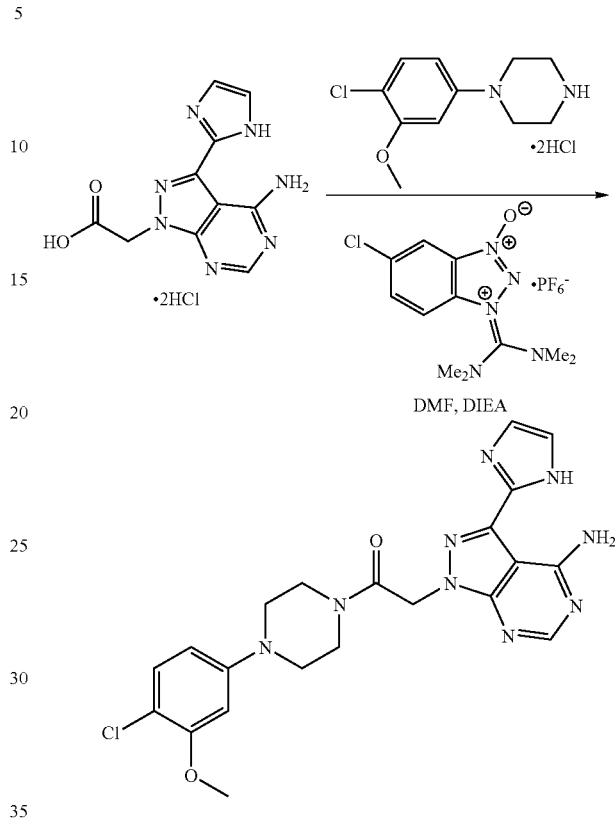

[4-Amino-3-(1H-imidazol-2-yl)pyrazolo[3,4-d]pyrimidin-1-yl]acetic acid dihydrochloride (79 g, 0.238 mol) and 1-(4-chloro-3-methoxyphenyl)piperazine dihydrochloride (71.3 g, 0.238 mol) were suspended in anhydrous DMF (793 mL) and cooled in an ice bath. N,N-diisopropylethylamine (290 mL, 1.67 mol) was added and the mixture was stirred at room temperature until all solids dissolved to form a brown solution. HCTU (113.23 g, 0.273 mol) was added in portions over 10 min while maintaining the internal temperature below 20° C. After 3 h, the reaction mixture was poured slowly into a flask of vigorously stirred ice water (6 L) to give a suspension, which was stirred for 1 h, filtered, and washed with saturated NaHCO$_3$ (500 mL×2) and water (500 mL×2). The solid was purified by trituration in refluxing MeCN (2×500 mL) to provide 2-[4-amino-3-(1H-imidazol-2-yl)-pyrazolo[3,4-d]pyrimidin-1-yl]-1-[4-(4-chloro-3-methoxyphenyl)piperazin-1H-yl]ethanone (90.5 g, 81% yield, >98% pure by LC-MS). $^1$H NMR (400 MHz, d$_6$-DMSO) δ 13.0 (s, 1H), 10.14 (d, 1H, J=3.7 Hz), 8.16 (s, 1H), 7.95 (d, 1H, d, J=3.7 Hz), 7.25 (dd, 1H, J=1.03 and 1.36 Hz), 7.20 (d, 1H, J=8.8 Hz), 7.16 (s, 1H), 6.70 (d, 1H, J=2.4 Hz), 6.52 (dd, 1H, J=2.4 and 8.8 Hz), 5.37 (s, 2H), 3.83 (s, 3H), 3.74 (t, 2H, J=4.8 Hz), 3.58 (t, 2H, J=4.8 Hz), 3.28 (t, 2H, J=4.8 Hz), 3.17 (t, 2H, J=4.8 Hz). $^{13}$C NMR (100.6 MHz, d$_6$-DMSO) δ 165.3, 159.0, 157.3, 155.7, 155.5, 151.6, 141.2, 136.6, 130.3, 128.7, 119.0, 111.9, 109.0, 101.9, 98.0, 56.7, 49.4, 48.9, 48.8, 44.7, 42.1; IR (KBr) 3219, 2937, 1682, 1638, 1594, 1567 cm$^{-1}$; MS (ES) m/z 468.1(M+H$^+$). Anal. Calcd for C$_{21}$H$_{22}$N$_9$O$_2$Cl-0.85 H$_2$O: C, 52.20; H, 4.94; N, 26.09; Cl, 7.34. Found: C, 51.92; H, 4.68; N, 26.44; Cl, 7.18.

Step 6: 2-[4-Amino-3-(1H-imidazol-2-yl)-pyrazolo[3,4-d]pyrimidin-1-yl]-1-[4-(4-chloro-3-methoxyphenyl)piperazin-1-yl]ethanone dihydrochloride salt

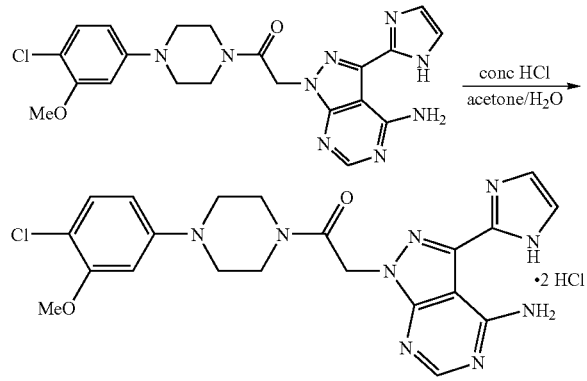

To a mixture of 2-[4-amino-3-(1H-imidazol-2-yl)-pyrazolo[3,4-d]pyrimidin-1-yl]-1-[4-(4-chloro-3-methoxyphenyl)piperazin-1-yl]ethanone (50 g, 0.1068 mol), H$_2$O (250 mL), and acetone (750 mL) at 60° C. was added concentrated HCl (22.3 mL, 0.267 mol, 2.50 equiv) dropwise to give a brown solution. After 90 min, a thick tan suspension formed. The suspension was diluted to a final concentration of 0.03 M by dropwise addition of acetone (2.1 L) while maintaining the internal temperature between 58° C. to 62° C. The resulting mixture was stirred at 60° C. for another 90 min, cooled to room temperature, and filtered. The solid was washed with acetone (60 mL×2) and dried in vacuo to afford 2-[4-amino-3-(1H-imidazol-2-yl)-pyrazolo[3,4-d]pyrimidin-1-yl]-1-[4-(4-chloro-3-methoxyphenyl)piperazin-1-yl]ethanone dihydrochloride salt (49.2 g, 80% yield, >99% pure by LC-MS) as fine tan prisms. $^1$H NMR (400 MHz, d$_6$-DMSO) δ 13.45 (s, 1H), 11.92 (s, 1H), 9.43 (s, 1H), 8.50 (s, 1H), 7.33 (s, 2H), 7.22 (d, 1H, J=8.8 Hz), 6.72 (d, 1H, J=2.4 Hz), 6.55 (dd, 1H, J=2.4, 8.8 Hz), 5.54 (s, 2H), 3.84 (s, 3H), 3.76 (t, 2H, J=4.8 Hz), 3.61 (t, 2H, J=4.8 Hz), 3.31 (t, 2H, J=4.8 Hz), 3.20 (t, 2H, J=4.8 Hz). MS (ES) m/z 468.1(M+H$^+$). Anal. Calcd for C$_{21}$H$_{22}$N$_9$O$_2$Cl-2HCl-1.75H$_2$O: C, 44.07; H, 4.84; N, 22.02; Cl, 18.58. Found: C, 43.89; H, 4.48; N, 22.0; Cl, 18.26. KF (H$_2$O) Calcd for C$_{21}$H$_{22}$N$_9$O$_2$Cl-2HCl-1.75H$_2$O: 5.51%. Found: 5.14%.

Example 2

This example illustrates the preparation of 2-[4-amino-3-(1H-imidazol-2-yl)-pyrazolo[3,4-d]pyrimidin-1-yl]-1-[4-(4-chloro-3-methoxyphenyl)-2,2-dimethylpiperazin-1-yl]ethanone

Step 1: 4-(4-chloro-3-methoxy-phenyl)-3,3-dimethylpiperazine dihydrochloride

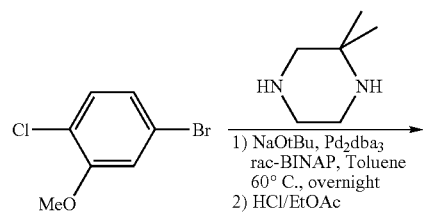

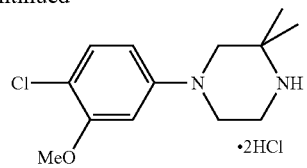

A mixture of 5-bromo-2-chloroanisole (3.70 g, 16.7 mmol, 1 equiv), 2,2-dimethyl-piperazine (2.2 g, 1.2 equiv) and rac-BINAP (1.04 g, 0.1 equiv) in toluene (35 mL) was degassed with compressed nitrogen for 5 min. To the mixture were added NaOt-Bu (2.3 g, 1.4 equiv) and Pd$_2$(dba)$_3$ (54 mg, 0.005 equiv). The resulting mixture was heated at 60° C. overnight and cooled to room temperature. EtOAc (~200 mL) was added and the mixture was filtered through celite. The filtrate was washed with saturated aqueous K$_2$CO$_3$ (200 mL), saturated aqueous NaHCO$_3$ (200 mL), and brine (200 mL) sequentially and then dried over magnesium sulfate. The resulting residue after evaporation was dissolved in EtOAc (100 mL) and treated with 2 N HCl in Et$_2$O (100 mL) at room temperature for 2 h. A solid was collected by filtration and dried in vacuo to afford 4-(4-chloro-3-methoxy-phenyl)-3,3-dimethylpiperazine dihydrochloride (4.0 g). MS (ES) m/z 255.1 (M+H$^+$).

Step 2: 2-[4-Amino-3-(1H-imidazol-2-yl)-pyrazolo[3,4-d]pyrimidin-1-yl]-1-[4-(4-chloro-3-methoxyphenyl)-2,2-dimethylpiperazin-1-yl]ethanone

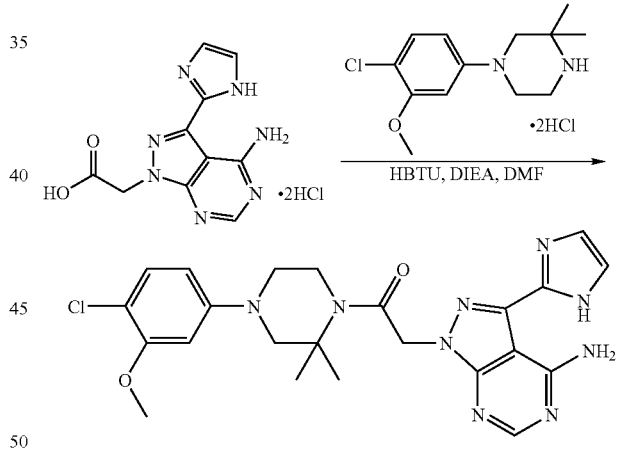

[4-Amino-3-(1H-imidazol-2-yl)pyrazolo[3,4-d]pyrimidin-1l-yl]acetic acid dihydrochloride (100 mg, 0.2 mmol) and 1-(4-chloro-3-methoxyphenyl)-3,3-dimethylpiperazine dihydrochloride (100 mg, 0.3 mmol) were suspended in anhydrous DMF (2.5 mL). N,N-Diisopropylethylamine (0.32 mL, 1 mmol) was added at 0° C. and the mixture was stirred at room temperature until all solids dissolved to give a brown solution. HBTU (114 mg, 0.3 mmol) was added. After 2 h, the reaction mixture was poured slowly into a flask of vigorously stirred ice-water (100 mL). The resulting suspension was extracted with dichloromethane (100 mL) and washed with saturated NaHCO$_3$ (100 mL), brine (100 mL) and evaporated. The residue was purified by flash column chromatography to afford 2-[4-amino-3-(1H-imidazol-2-yl)-pyrazolo[3,4-d]pyrimidin-1-yl]-1-[4-(4-chloro-3-methoxyphenyl)-2,2-dimethylpiperazin-1-yl]ethanone as a light tan solid (45 mg) after evaporation and drying in vacuo. $^1$H NMR (400 MHz, d$_6$-DMSO) δ 10.14 (d, 1H, J=3.6 Hz), 8.16 (s, 1H), 7.95 (d, 1H, d, J=3.6 Hz), 7.24 (s, 1H), 7.15 (s, 1H), 7.14 (d, 1H, J=8.8 Hz), 6.40 (d, 1H, J=2.4 Hz), 6.31 (dd, 1H, J=2.4 and 8.8 Hz), 5.29 (s, 2H), 3.90 (t, 2H, J=5.4 Hz), 3.84 (s, 3H), 3.46 (t, 2H, J=5.4 Hz), 3.30 (s, 2H), 1.38 (s, 6H). MS (ES) m/z 491.1 (M+H$^+$).

Example 3

This example illustrates the preparation of 2-[4-amino-3-(1H-imidazol-2-yl)-pyrazolo[3,4-d]pyrimidin-1-yl]-1-[4-(4-chloro-2-fluoro-5-methoxyphenyl)-piperazin-1-yl]ethanone

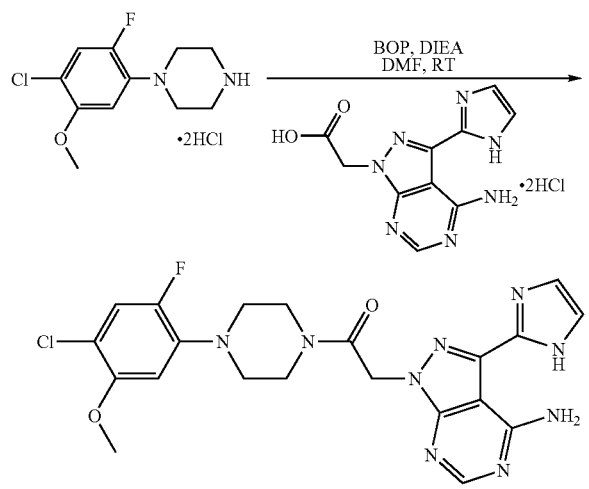

A mixture of 1-(4-chloro-2-fluoro-5-methoxyphenyl)-piperazine dihydrochloride salt (65.2 mg, 0.206 mmol, 1 equiv), [4-amino-3-(1H-imidazol-2-yl)-pyrazolo[3,4-d]pyrimidin-1-yl]acetic acid (50 mg, 1 equiv), BOP reagent (109 mg, 1.7 equiv) and N,N-diisopropylethylamine (0.165 mL, 5 equiv) in DMF (0.5 mL) was stirred at room temperature overnight. Reverse phase HPLC (acetonitrile-H$_2$O with 0.1% TFA as eluent) purification gave 2-[4-amino-3-(1H-imidazol-2-yl)-pyrazolo[3,4-d]pyrimidin-1-yl]-1-[4-(4-chloro-2-fluoro-5-methoxyphenyl)-piperazin-1-yl]ethanone. MS (ES) m/z 486.5 (M+H$^+$).

Example 4

This example illustrates the preparation of 2-[4-amino-3-(1H-imidazol-2-yl)-pyrazolo[3,4-d]pyrimidin-1-yl]-1-[4-(4-chloro-2-fluoro-5-methoxyphenyl)-2-methyl-piperazin-1-yl]ethanone

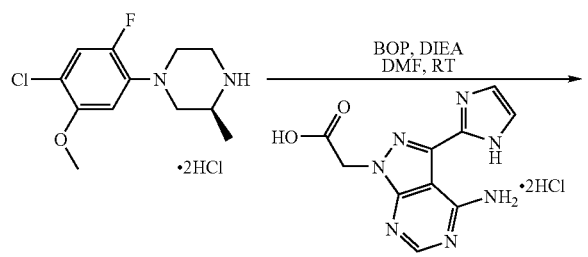

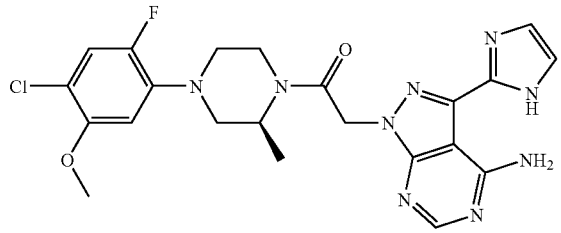

The title compound was prepared by a procedure analogous to that described in Example 3 using 1-(4-chloro-2-fluoro-5-methoxyphenyl)-3-methylpiperazine dihydrochloride. $^1$H NMR (400 MHz, d$_6$-DMSO) δ 14.20 (br, 2H), 10.28 (br, 1H), 8.15 (s, 1H), 7.93 (br s, 1H), 7.33 (d, 1H, J=11.6 Hz), 7.17 (br s, 1H), 6.71 (d, 1H, J=8.0 Hz), 5.44 (m, 1H), 5.21 (d, 1H, J=15.6 Hz), 4.54 (m, 0.5H), 4.39 (m, 0.5H), 4.19 (m, 0.5H), 3.97 (m, 0.5H), 3.84 (s, 3H), 3.56 (m, 0.5 Hz), 3.40 (m, 2H), 3.08 (m, 0.5H), 2.96 (m, 0.5H), 2.85 (m, 1H), 2.72 (m, 0.5H), 1.42 (d, 1H, J=6.0 Hz), 1.24 (d, 2H, J=6.8 Hz). MS (ES) m/z 500.5 (M+H$^+$).

Example 5

This example illustrates the preparation of 2-[4-amino-3-(1H-imidazol-2-yl)-pyrazolo[3,4-d]pyrimidin-1-yl]-1-[4-(4-chloro-2-fluorophenyl)-2-methyl-piperazin-1-yl]ethanone

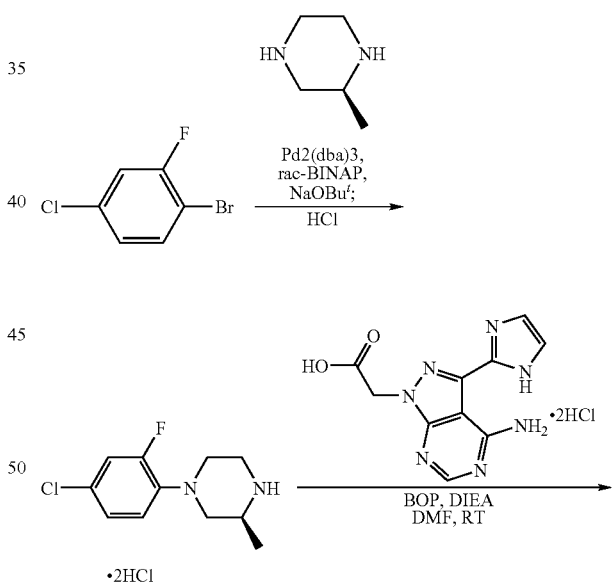

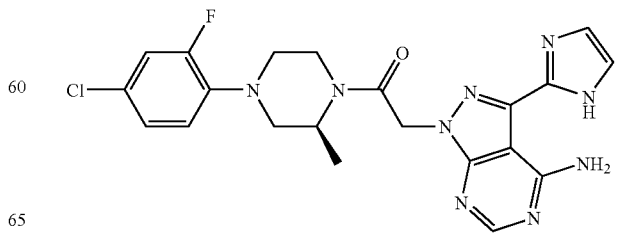

Step 1:
1-(4-chloro-2-fluoro-phenyl)-3-methylpiperazine

1-Bromo-4-chloro-2-fluorobenzene (5 g, 23.9 mmol, 1 equiv), of 2-methylpiperazine (2.8 g, 1.15 equiv), tris-benzylidineacetone dipalladium(0) (0.43 g, 0.05 equiv), rac-BINAP (0.89 g, 0.15 equiv), sodium tert-butoxide (3.2 g, 1.4 equiv) were slurried in toluene (60 mL), and the mixture was heated at 65° C. overnight. After cooling to room temperature, ethyl acetate (100 mL) was added. The black precipitate was removed by filtration. The filtrate was washed with 3N potassium carbonate solution twice. The organic phase was dried over sodium sulfate and neutralized with 2N HCl-ether. The solid was collected by filtration, washed with ether and dried in vacuo to give 1-(4-chloro-2-fluorophenyl)-3-methylpiperazine as a dihydrochloride salt.

Step 2: The title compound was prepared by a procedure analogous to that described in Example 3 using 1-(4-chloro-2-fluorophenyl)-3-methylpiperazine. $^1$H NMR (400 MHz, CDCl$_3$) δ 10.38 (br, 1H), 10.26 (br, 1H), 8.32 (s, 1H), 7.24 (m, 2H), 7.17 (s, 1H), 7.07 (s, 1H), 7.04 (d, 2H, J=2 Hz), 6.80 (t, 1H, J=8.8 Hz), 5.93 (br s, 1H), 5.24 (m, 2H), 4.81 (s, 0.5H), 4.47 (d, 0.5H, J=12 Hz), 4.20 (s, 0.5H), 3.68 (m, 1H), 3.31 (m, 2H), 2.88 (t, 1H, J=16 Hz), 2.76 (dd, 1H, J=12, 3.6 Hz), 1.50 (d, 1.5H, J=5.2 Hz), 1.39 (d, 1.5H, J=6.4 Hz). MS (ES) m/z 470.5 (M+H$^+$).

Example 6

This example illustrates the preparation of 2-[4-amino-3-(1H-imidazol-2-yl)-pyrazolo[3,4-d]pyrimidin-1-yl]-1-[4-(4-chloro-3-ethoxyphenyl)-piperazin--yl]ethanone

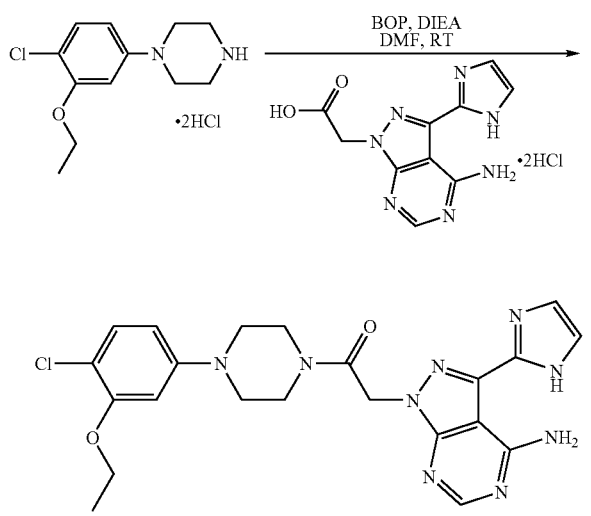

The title compound was prepared by a procedure analogous to that described in Example 3 using 1-(4-chloro-3-ethoxyphenyl)piperazine dihydrochloride. $^1$H NMR (400 MHz, d$_6$-DMSO) δ 14.20 (br, 1H), 10.13 (br, 1H), 8.15 (s, 1H), 7.98 (d, 1H, J=4 Hz), 7.25 (S, 1H,), 7.19 (d, 1H, J=8.8 Hz), 7.15 (s, 1H), 6.68 (d, 1H, J=2.4 Hz), 6.51 (dd, 1H, J=8.8, 2.8 Hz), 5.36 (s, 2H), 4.09 (q, 2H, J=6.4 Hz), 3.73 (br, 2H), 3.57 (br, 2H), 3.26 (br, 2H), 3.15 (br, 2H), 1.34 (t, 3H, J=6.8 Hz). MS (ES) m/z 482.5 (M+H$^+$).

Example 7

This example illustrates the preparation of 2-[4-amino-3-(1H-imidazol-2-yl)-pyrazolo[3,4-d]pyrimidin-1-yl]-1-[4-(4-chloro-3-methoxyphenyl)-2-methyl-piperazin-1-yl]ethanone

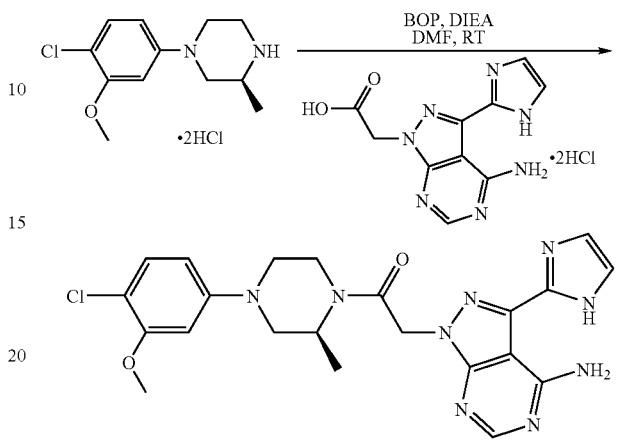

The title compound was prepared by a procedure analogous to that described in Example 3 using 1-(4-chloro-3-methoxyphenyl)-3-methylpiperazine dihydrochloride. $^1$H NMR (400 MHz, d$_6$-DMSO) δ 14.4 (br, 1H), 10.13 (s, 1H), 8.16 (s, 1H), 7.99 (s, 1H), 7.25 (t, 1H, J=1.2Hz), 7.19 (d, 1H, J=8Hz), 7.15 (s, 1H), 6.64 (s, 1H), 6.50 (m, 1H), 5.51-5.21 (m, 2H), 4.49 (s, 0.5H), 4.38 (s, 0.5H), 4.15 (m, 0.5H), 3.98 (m, 0.5H), 3.83 (s, 3H), 3.70 (m, 1H), 3.55 (m, 1H), 3.29 (s, 1H), 3.08-2.85 (m, 2H), 1.37 (d, 1.5H, J=6.0 Hz), 1.18 (d, 1.5H, J=6.4 Hz). MS (ES) m/z 482.2 (M+H$^+$).

Example 8

This example illustrates the preparation of 2-[4-amino-3-(1H-imidazol-2-yl)-pyrazolo[3,4-d]pyrimidin-1-yl]-1-[4-(4-chlorophenyl)-2-methylpiperazin-1-yl]ethanone

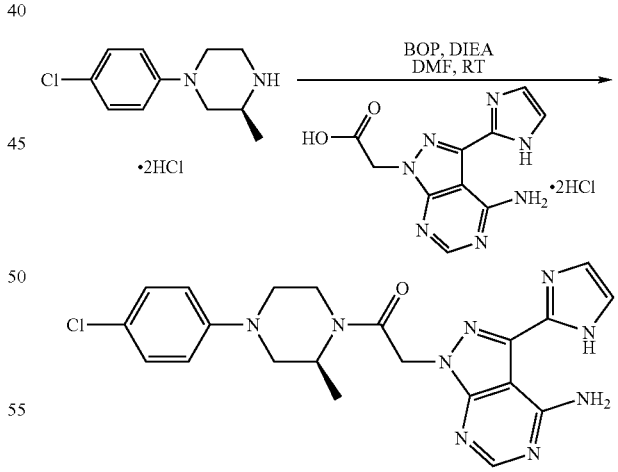

The title compound was prepared by a procedure analogous to that described in Example 3 using 1-(4-chlorophenyl)-3-methylpiperazine dihydrochloride. $^1$H NMR (400 MHz, d$_6$-DMSO) δ 11.96 (br, 1H), 9.62 (s, 1H), 8.52 (s, 1H), 7.48 (s, 1H), 7.35 (s, 1H), 7.30 (s, 1H), 7.22 (t, 2H, J=2.4 Hz), 6.96 (t, 2H, J=8Hz), 5.50 (m, 2H), 4.45 (m, 0.5H), 4.15 (m, 0.5H), 3.90 (m, 0.5H), 3.55 (m, 2H), 2.8-3.14 (m, 2H), 2.60 (m, 0.5 Hz), 1.89 (s, 1H), 1.39 (d, 1.5H, J=6.0 Hz), 1.18 (d, 1.5H, J=6.8 Hz). MS (ES) m/z 452.1 (M+H$^+$).

Example 9

This example illustrates the preparation of 2-[4-amino-3-(1H-imidazol-2-yl)-pyrazolo[3,4-d]pyrimidin-1-yl]-1-[4-(4-chlorophenyl)piperazin-1-yl]ethanone

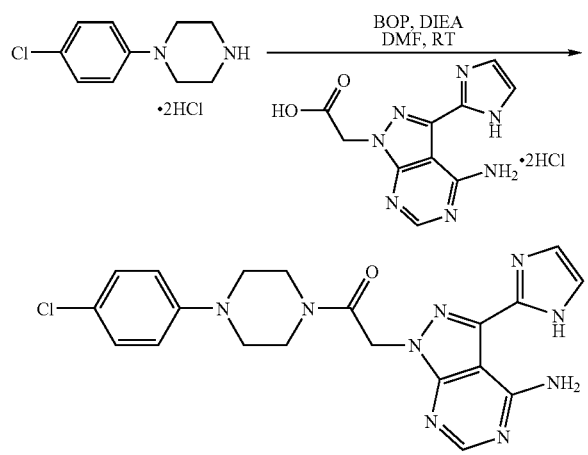

The title compound was prepared by a procedure analogous to that described in Example 3 using 1-(4-chlorophenyl) piperazine dihydrochloride. MS (ES) m/z 438.1 (M+H$^+$).

Example 10

This example illustrates the preparation of 2-[4-amino-3-(1H-imidazol-2-yl)-pyrazolo[3,4-d]pyrimidin-1-yl]-1-[4-(4-chloro-3-ethoxyphenyl)-2-methylpiperazin-1-yl]ethanone

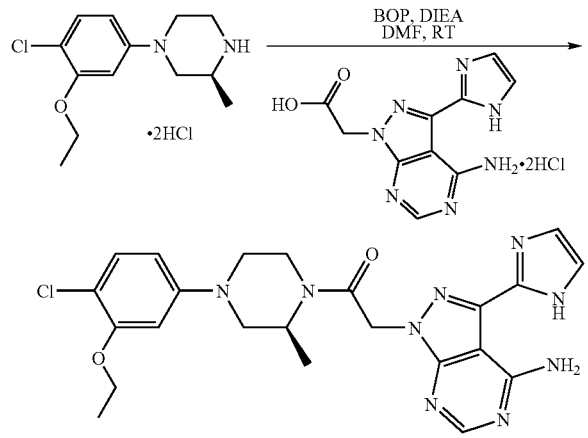

The title compound was prepared by a procedure analogous to that described in Example 3 using 1-(4-chloro-3-ethoxyphenyl)-3-methylpiperazine dihydrochloride. $^1$H NMR (400 MHz, d$_6$-DMSO) δ 14.4 (br, 1H), 10.15 (s, 1H), 8.16 (s, 1H), 7.98 (s, 1H), 7.25 (s, 1H), 7.18 (d, 1H, J=8.8 Hz), 7.15 (s, 1H), 6.62 (s, 1H,), 6.50 (m, 1H), 5.51-5.25 (m, 2H), 4.48 (s, 0.5H), 4.38 (s, 0.5H), 4.09 (m, 2.5H), 3.93 (m, 0.5H), 3.68-3.51 (m, 2H), 3.07-2.75 (m, 2.5H), 2.61 (m, 0.5H), 1.33(t, 3H, J=6.8 Hz), 1.17(d, 3H, J=7.2 Hz). MS (ES) m/z 496.5 (M+H$^+$).

Example 11

This example illustrates the preparation of 2-[4-amino-3-(1H-imidazol-2-yl)-pyrazolo[3,4-d]pyrimidin-1-yl]-1-[4-(4-chloro-3-trifluoromethoxyphenyl)piperazin-1-yl]ethanone

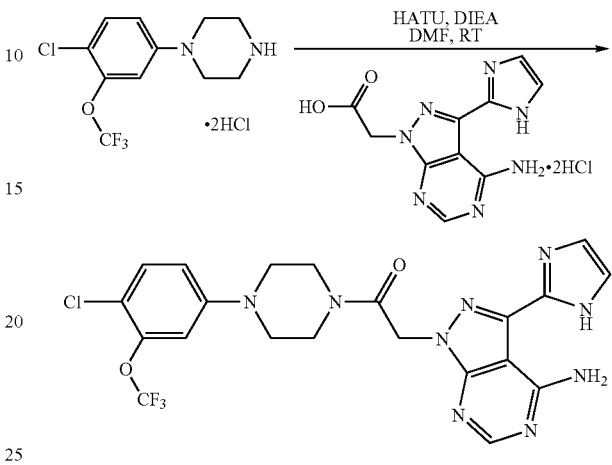

A mixture of 1-(4-chloro-3-trifluoromethoxyphenyl)piperazine didydrochloride salt (70 mg, 0.198 mmol, 1 equiv), [4-amino-3-(1H-imidazol-2-yl)-pyrazolo[3,4-d]pyrimidin-1-yl]acetic acid (96 mg, 1 equiv), HATU (98 mg, 1.3 equiv) and N,N-diisopropylethylamine (0.276 mL, 8 equiv) in DMF (0.5 mL) was stirred at room temperature for 3 h. The reaction mixture was diluted with ethyl acetate, washed with saturated aqueous sodium bicarbonate, dried over sodium sulfate, and purified by TLC to give 2-[4-amino-3-(1H-imidazol-2-yl)-pyrazolo[3,4-d]pyrimidin-1-yl]-1-[4-(4-chloro-3-trifluoromethoxyphenyl)piperazin-1-yl]ethanone. $^1$H NMR (400 MHz, CD$_3$OD) δ 8.18 (s, 1H), 7.39 (s, 1H,), 7.18 (d, 2H, J=8.8 Hz), 6.95 (s, 2H), 5.40 (s, 2H), 3.85 (m, 4H), 3.25 (m, 4H). The three remaining protons (from the amino group and the imidazole ring) were not observed due to the use of CD$_3$OD as solvent. MS (ES) m/z 522.1 (M+H$^+$).

Example 12

This example illustrates the preparation of 2-[4-amino-3-(1H-imidazol-2-yl)-pyrazolo[3,4-d]pyrimidin-1-yl]-1-[4-(4-chloro-2-fluorophenyl)piperazin-1-yl]ethanone

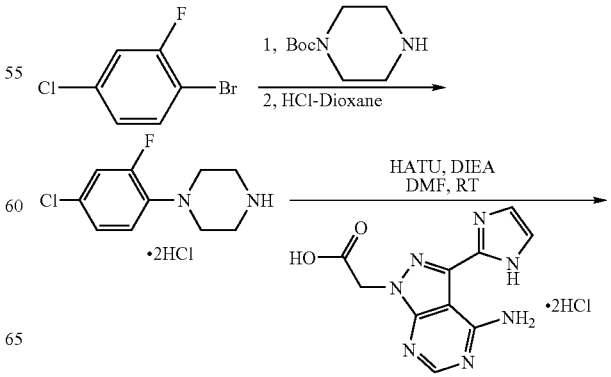

-continued

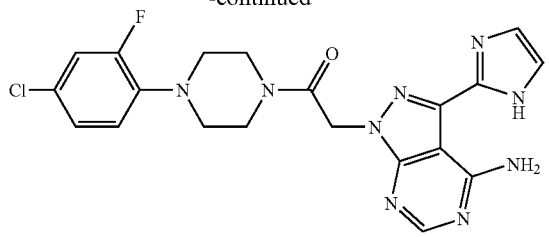

Step 1: 1-(4-chloro-2-fluorophenyl)piperazine

1-Bromo-4-chloro-2-fluorobenzene (5 g, 23.9 mmol, 1 equiv), piperazine-1-carboxylic acid teat-butyl ester (5.3 g, 1.15 equiv), tris-benzylidineacetone dipalladium(0) (0.43 g, 0.05 equiv), rac-BINAP (0.89 g, 0.15 equiv), sodium tert-butoxide (3.2 g, 1.4 equiv) were slurried in toluene (60 mL), and the mixture was heated at 65° C. overnight. After cooling to room temperature, ethyl acetate (100 mL) was added. The black precipitate was removed by filtration. The filtrate was washed with 3N potassium carbonate solution twice. The organic phase was dried over sodium sulfate, concentrated and treated with 4N HCl in dioxane. The solid was collected by filtration, washed with ether, and dried under high vacuum to give 1-(4-chloro-2-fluorophenyl)piperazine as a dihydrochloride salt.

Step 2: The title compound was prepared by a procedure analogous to that described in Example 11 using 1-(4-chloro-2-fluorophenyl)piperazine dihydrochloride. $^1$H NMR (400 MHz, CD$_3$OD) δ 8.16 (s, 1H), 7.19 (s, 1H), 7.1-7.17 (m, 3H), 7.05 (m, 1H), 5.40 (s, 2H0, 3.85 (m, 2H), 3.75 (m, 2H), 3.18 (m, 2H), 3.07 (m, 2H). The three remaining protons (from the amino group and the imidazole ring) were not observed due to the use of CD$_3$OD as solvent. MS (ES) m/z 456.1 (M+H$^+$).

Example 13

This example illustrates the evaluation of the biological activity associated with compounds of interest of the invention.

Materials and Methods
A. Cells
 1. CCR1 Expressing Cells
  a) THP-1 Cells

THP-1 cells were obtained from ATCC (TIB-202) and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% CO$_2$/95% air, 100% humidity at 37° C. and subcultured twice weekly at 1:5 (cells were cultured at a density range of 2×10$^5$ to 2×10$^6$ cells/mL) and harvested at 1×10$^6$ cells/mL. THP-1 cells express CCR1 and can be used in CCR1 binding and functional assays.

2. Chemotaxis Assays
  Identification of Inhibitors of CCR1

One of the primary functions of chemokines is their ability to mediate the migration of chemokine receptor-expressing cells, such as white blood cells. To confirm that a compound of interest inhibited not only CCR1 specific binding and signaling (at least as determined by calcium mobilization assays), but also CCR1 mediated migration, a chemotaxis assay was employed. THP-1 myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were place in the top compartment of a microwell migration chamber, 5 μm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS. CCR1 chemokine ligands (i.e., MIP-1α, CCL15/Leukotactin; R&D Systems; Minneapolis, Minn.) are used to evaluate compound mediated inhibition of CCR1 mediated migration. Other chemokines (i.e., SDF-1α; R&D Systems; Minneapolis, Minn.) are used as specificity controls. The lower chamber was loaded with 29 μl of chemokine (i.e., 0.1 nM CCL15/Leukotactin) and varying amounts of compound; the top chamber contained 100,000 THP-1 or monocyte cells in 20 μl. In the absence of inhibitor, cells will migrate to the lower chamber in response to the chemokine agonist; if a compound inhibited CCR1 function, then the majority of cells will remain in the upper chamber. To ascertain a compound of interest's affinity for CCR1 as well as to confirm its ability to inhibit CCR1 mediated cell migration, inhibitory activity was titered over a 1×10$^{-10}$ to 1×10$^{-4}$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate IC$_{50}$ values. IC$_{50}$ values are those compound concentrations required to inhibit the number of cells responding to a CCR1 agonist by 50%.

3. In Vivo Efficacy
  a) Rabbit Model of Destructive Joint Inflammation

A rabbit LPS study can be conducted essentially as described in Podolin, et al. ibid., Female New Zealand rabbits (approximately 2 kilograms) are treated intra-articularly in both knees with LPS (10 ng). The compound of interest (e.g. formulated in 1% methocel) or vehicle (1% methocel) are dosed orally at a 5 ml/kg dose volume at two times (2 hours before the intra-articular LPS injection and 4 hours after the intra-articular LPS injection). Sixteen hours after the LPS injection, knees are lavaged and cells counts performed. Beneficial effects of treatment are determined by reduction in the number of inflammatory cells recruited to the inflamed synovial fluid of the knee joints. Treatment with the compound of interest results in a significant reduction in recruited inflammatory cells.

b) Evaluation of a Compound of Interest in a Rat Model of Collagen Induced Arthritis A 17 day developing type II collagen arthritis study can be conducted to evaluate the effects of a compound of interest on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3):857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A compound of interest is dosed daily in a sub-cutaneous manner from day 0 till day 17 at a efficacious dose. Caliper measurements of the ankle joint diameter are taken, and reduced joint swelling is taken as a measure of efficacy.

c) Rat Model of Ovariectomy Induced Osteoporosis

A rat model of ovariectomy induced osteoporosis can be conducted essentially as Dunstan et al, (1999) *J. Bone and Min Res.* 14:953. Young female Sprague-Dawley rats (180-200 g) are sham operated or ovariectomized (OVX). Within 7 days of the operation, daily oral doses of CCR1 antagonist or vehicle alone (sesame oil) are commenced. After two weeks of dosing, the rats are euthanized and serum levels of osteoclast and osteoblast biomarkers (C-telopeptide and MID osteocalcin, respectively) are analyzed. Additionally, the femur and tibia are removed for histopathological examination with H&E and/or TRAP staining.

d) The Modified Radl TGM1 Model of Myeloma Bone Disease

Myeloma bone disease may be studied as further described in Oyajobi et al, *Mol Cancer Ther,* 2007, 6:1701-1708. Animal studies are conducted using 6- to 9-week-old female C57BL/KaLwRijHsd mice (Harlan). Myeloma lesions are induced in mice by i.v. inoculation of $10^6$ viable 5TGM1-eGFP H1.1+ cells or parental 5TGM1 cells through tail veins. The compound of interest (e.g. formulated in 100% sesame oil) or vehicle (100% sesame oil) are dosed orally at a 2.5 ml/kg dose volume twice daily for 4 weeks. Body weights of animals are determined at baseline and weekly thereafter. At the end of 4 weeks, whole mice are imaged and, immediately after sacrifice, skeletons and visceral organs (spleens, livers, kidneys, gonads, brains, lungs, and hearts) are dissected out and imaged for fluorescent tumor foci to assess tumor burden.

In Table 2 (below), structures and activity are provided for representative compounds described herein. Activity is provided as follows for the chemotaxis assay as described above: +, 10 nM <$IC_{50}$≦150 nM; ++, 1 nM <$IC_{50}$≦10 nM; and +++, $IC_{50}$≦1 nM.

TABLE 2-continued

| Structure |
|---|
| 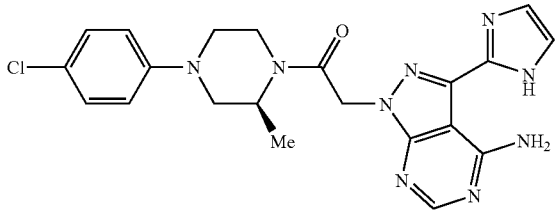 1.008/++ |
| 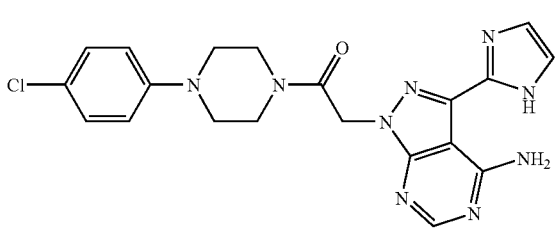 1.009/+ |
| 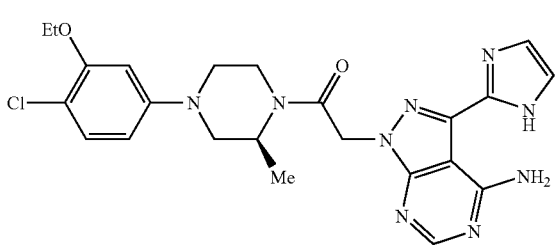 [SMILES: COc1cc(N2CCN(C(=O)Cn3nc(-c4ncc[nH]4)c4c(N)ncnc43)[C@@H](C)C2)c(F)cc1Cl] 1.010/+++ |
| 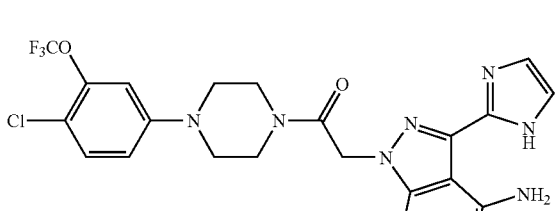 1.011/+ |
| 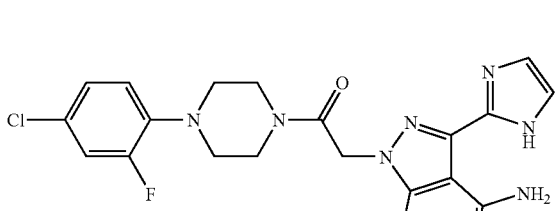 1.012/++ |

In direct comparisions, compounds 1.001, 1.003, 1.004, 1.006, 1.007, 1.010 and 1.011 of the present invention provided activity that was at least an order of magnitude better than activity demonstrated by the related compounds tested (imidazole-substituted pyrido[4,3-b]pyrazoles in related U.S. application Ser. No. 12/124,894. For example, in the chemotaxis assay,

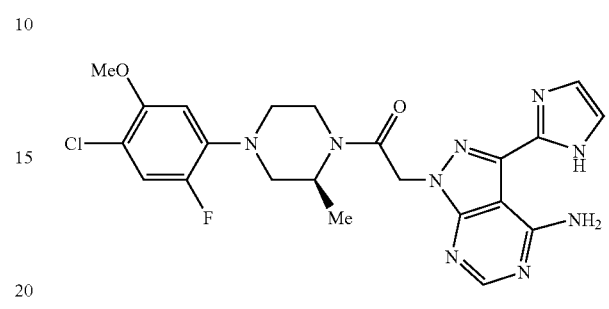

provided an $IC_{50}$ that was an order of magnitude lower than

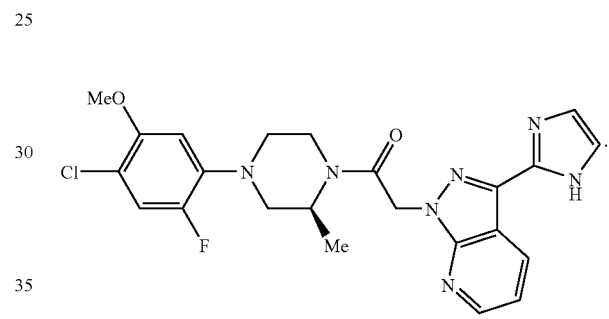

The invention having now been described by way of written description and example, those of skill in the art will recognize that the invention can be practiced in a variety of embodiments and that the foregoing description and examples are for purposes of illustration and not limitation of the following claims.

What is claimed is:

1. A compound having the formula:

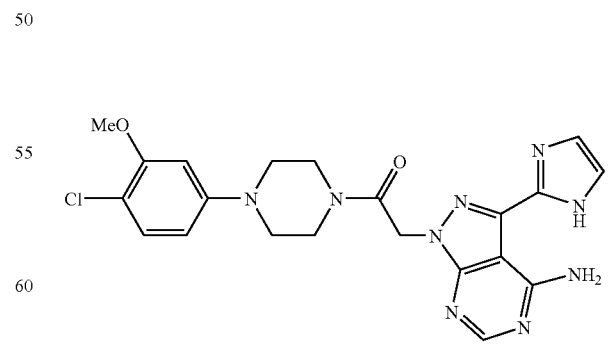

or a pharmaceutically acceptable salt thereof.

2. The compound of claim 1, having the formula:
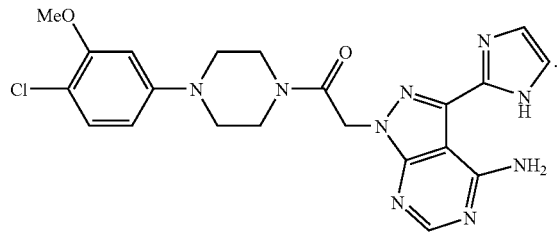 [SMILES: COc1cc(N2CCN(C(=O)Cn3nc(-c4ncc[nH]4)c4c(N)ncnc43)CC2)ccc1Cl]
3. The compound of claim 1, having the formula:
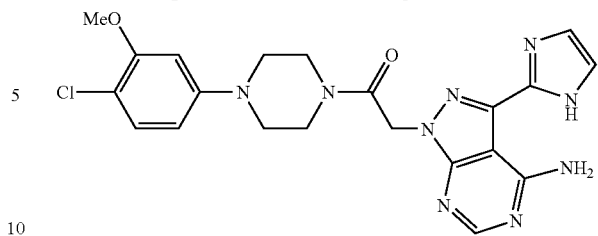
in a pharmaceutically acceptable salt form.
4. The compound of claim 3, wherein said salt form is a hydrochloride salt form.
* * * * *